(12) United States Patent
Minemura et al.

(10) Patent No.: US 9,381,264 B2
(45) Date of Patent: Jul. 5, 2016

(54) STEAM STERILIZER

(75) Inventors: Eiichi Minemura, Chikuma (JP); Haruo Machida, Chikuma (JP); Hiroshi Karasawa, Chikuma (JP)

(73) Assignee: Sakura Seiki Co., Ltd., Nagano (JP)

( * ) Notice: Subject to any disclaimer, the term of this patent is extended or adjusted under 35 U.S.C. 154(b) by 24 days.

(21) Appl. No.: 14/381,185

(22) PCT Filed: Mar. 2, 2012

(86) PCT No.: PCT/JP2012/055354
§ 371 (c)(1),
(2), (4) Date: Aug. 26, 2014

(87) PCT Pub. No.: WO2013/128626
PCT Pub. Date: Sep. 6, 2013

(65) Prior Publication Data
US 2015/0023841 A1    Jan. 22, 2015

(51) Int. Cl.
*A61L 2/07* (2006.01)
*A61L 11/00* (2006.01)
*B09B 3/00* (2006.01)

(52) U.S. Cl.
CPC . *A61L 2/07* (2013.01); *A61L 11/00* (2013.01); *B09B 3/0091* (2013.01); *A61L 2202/14* (2013.01); *A61L 2202/15* (2013.01)

(58) Field of Classification Search
CPC .......................................................... A61L 2/07
USPC ................................................. 422/107, 292
See application file for complete search history.

(56) References Cited

U.S. PATENT DOCUMENTS 4,759,909 A * 7/1988 Joslyn ....................... A61L 2/07
                                                                422/110

FOREIGN PATENT DOCUMENTS

| JP | 2000199490 | 7/2000 |
|----|------------|--------|
| JP | 2010253036 | 11/2010 |
| WO | WO-9006779 | 6/1990 |

OTHER PUBLICATIONS

Enlgish language machine translation of JP 2010-253036 A, inventor: Takahashi et al., published Nov. 2010.*
Sakura Seiki Co., Ltd., International Search Report mailed Apr. 3, 2012 for PCT/JP2012/055354.

* cited by examiner

*Primary Examiner* — Sean E Conley
(74) *Attorney, Agent, or Firm* — Blakely Sokoloff Taylor & Zafman LLP

(57) ABSTRACT

A steam sterilizer includes a sterilization tank configured to house an object to be sterilized and perform sterilization on the object to be sterilized by maintaining supplied steam at a predetermined temperature and under a predetermined pressure; a steam-supplying pipe configured to supply the steam into the sterilization tank; a steam-supplying pipe valve configured to control an amount of steam flow flowing through the steam-supplying pipe, wherein the steam-supplying pipe is provided so as to have a diameter that allows a pressure-increase rate of 100 kPa/min or more in the sterilization tank; and a control unit configured to control the steam-supplying pipe valve to be fully opened, in a conditioning process for repeatedly performing introduction and discharge of the steam in and from the sterilization tank and to control the steam-supplying pipe valve so as to supply a predetermined amount of steam, in a sterilization process after the conditioning process.

8 Claims, 5 Drawing Sheets

STEAM STERILIZER

CROSS-REFERENCE TO RELATED APPLICATION

This application is a non-provisional application claiming the benefit of International Patent Application No. PCT/JP2012/055354, filed Mar. 2, 2012.

TECHNICAL FIELD

The present invention relates to a steam sterilizer for sterilizing an object to be sterilized with steam.

BACKGROUND ART

In hospitals and the like, sterilization processing is required to be performed on objects to be sterilized, such as a bandage for treatment, a scalpel, a pair of forceps, and a surgical gown, which need to be sterilized. The steam sterilizer including a pressure vessel that houses the objects to be sterilized is often used for sterilizing such objects to be sterilized as described above.

General steam sterilizer acts so as to sterilize the object to be sterilized by introducing saturated steam into the pressure vessel to pressurize and heat it, and keeping a predetermined pressure and temperature for a predetermined time (refer to, for example, patent literature 1).

The steam sterilizer described in the patent literature 1 is the pressure vessel having a double-can structure in which a sterilization chamber that houses the object to be sterilized is formed of an inner can and an outer can. The portion between the inner can and the outer can of the pressure vessel is a jacket portion, and the saturated steam is introduced into the jacket portion. The inner can is heated by the saturated steam introduced into the jacket portion.

Furthermore, the saturated steam is introduced into an inside of the inner can. The inner can is pressurized and heated up to the predetermined pressure with the saturated steam introduced, and heated up to the predetermined temperature by the jacket portion around the inner can.

The inner can is kept at the predetermined pressure and the predetermined temperature with the saturated steam for the predetermined time, and thus the sterilization is performed on the object to be sterilized housed in the inner can. After the elapse of the predetermined time, a gas-discharge process for discharging the saturated steam from the inner can is executed. In the inner can set in a vacuum state by the gas-discharge process, moisture adhering to the object to be sterilized is evaporated and dried.

CITATION LIST

Patent Literature

PTL 1: Japanese Patent Laid-Open No. 2000-199490

SUMMARY OF THE INVENTION

Technical Problem

Generally, in a sterilization operation process using a steam sterilizer, the reduction of a sterilization operation time is desired, but since a sterilization time when an object to be sterilized is brought into contact with steam, a drying time for drying the object to be sterilized after the sterilization and the like are previously set as a sterilization condition, such times cannot be reduced. However, since a steam-supply time or a steam-discharge time would have directly nothing to do with the sterilization condition, these times may be reduced.

Meanwhile, if the steam-supply time and the steam-discharge time are simply tried to be reduced, the increase in diameters of a supply pipe and a discharge pipe speeds up the supply and discharge of the steam, and thus the supply time and the discharge time can be reduced.

On the other hand, in order to obtain a preferable temperature distribution, the steam supply speed at the time of a sterilization process is slowed down, and thus the temperature is required to gradually approach a set temperature at the time of the sterilization. Therefore, a problem occurs in which, simply when the diameters of the steam-supplying pipe and the steam discharge pipe are increased in order to reduce the steam-supply time and the steam-discharge time, the supply speed cannot be appropriately set, and thus the preferable temperature distribution cannot be set (the temperature may vary depending on a location in the sterilization tank).

Accordingly, the present invention has been made in order to solve the above-described problem, and an object of the present invention is to provide the steam sterilizer capable of achieving an appropriate distribution while reducing the sterilization operation time.

Solution to Problem

A steam sterilizer according to the present invention includes a sterilization tank configured to house an object to be sterilized and perform sterilization on the object to be sterilized by maintaining supplied steam at a predetermined temperature and a predetermined pressure; a steam-supplying pipe configured to supply the steam into the sterilization tank; a steam-supplying pipe valve configured to control an amount of steam flow flowing through the steam-supplying pipe, wherein the steam-supplying pipe is provided so as to have a diameter that allows a pressure-increase rate of 100 kPa/min or more in the sterilization tank; and a control unit configured to control the steam-supplying pipe valve to be fully opened, in a conditioning process for repeatedly performing introduction and discharge of the steam in and from the sterilization tank and to control the steam-supplying pipe valve so as to supply a predetermined amount of steam, in a sterilization process after the conditioning process.

By adoption of the above-described configuration, it is possible to adjust the diameter of the steam-supplying pipe so as to increase pressure as quickly as possible in accordance with a shape and volume of a pressure vessel. Therefore, in a conditioning process, when a steam-supplying pipe valve is fully opened, the steam-supply time can be reduced in the conditioning process. On the other hand, in a sterilization process, by controlling a level of opening the steam-supplying pipe valve so as to be a predetermined amount of a steam supply, it is possible to realize an appropriate temperature-rising rate and to thereby achieve a preferable temperature distribution.

Furthermore, the steam sterilizer may include a temperature sensor configured to measure an inner temperature of the sterilization tank; wherein, in the sterilization process after the conditioning process, the control unit is configured to control the steam-supplying pipe valve on the basis of the temperature detected by the temperature sensor.

According to the configuration described above, since an amount of the steam supply can be controlled on the basis of the temperature in the sterilization tank, the temperature distribution therein can be appropriately realized.

Moreover, the sterilization tank is provided inside an inner can of a pressure vessel having a double-can structure including the inner can and an outer can; a jacket portion is provided between the inner can and the outer can; the steam-supplying pipe is connected so as to introduce the steam into the jacket portion; a connection pipe for connecting the jacket portion with the inner can is provided in order to introduce, into the inner can, the steam introduced into the jacket portion; a connection-pipe valve for controlling an amount of steam flow flowing through the connection pipe is provided; a jacket portion temperature sensor is provided for measuring an inner temperature of said jacket portion, and in the sterilization process after the conditioning process, the control unit is configured to control the steam-supplying pipe valve on the basis of the temperature detected by the jacket portion temperature sensor.

As described above, even when the pressure vessel having the double-can structure is adopted, an appropriate temperature distribution can be realized in the inner can by controlling of the temperature-rising rate in the jacket on the basis of the temperature in the jacket.

In addition, the sterilization tank is provided inside an inner can of a pressure vessel having a double-can structure including the inner can and an outer can; a jacket portion is provided between the inner can and the outer can; the steam-supplying pipe is connected so as to introduce the steam into the jacket portion; a connection pipe for connecting the jacket portion with the inner can is provided in order to introduce, into the inner can, the steam introduced into the jacket portion; a connection-pipe valve for controlling an amount of steam flow flowing through the connection pipe is provided; an inner can temperature sensor for measuring an inner temperature of the inner can is provided; a jacket portion temperature sensor is provided for measuring an inner temperature of the jacket portion, and in the sterilization process after the conditioning process, the control unit is configured to control the steam-supplying pipe valve such that temperature difference between a temperature detected by the inner can temperature sensor and a temperature detected by the jacket portion temperature sensor is within a predetermined range.

As described above, even when the pressure vessel having the double-can structure is adopted, an appropriate temperature distribution can be realized in the inner can by controlling of the temperature-rising rate in the jacket on the basis of the temperature difference between the jacket portion and the inner can.

Furthermore, the control unit may be configured to fully open said connection-pipe valve in the sterilization process after the conditioning process.

With the arrangement, since the steam introduced into the jacket portion is controlled without controlling a circulation of the steam from the jacket portion into the inner can, the temperature-rising rate can be controlled by considering the jacket portion and the inner can as one body, and thus the generation of overly heated steam caused by a high temperature of the jacket portion can be prevented.

Moreover, a condensing device for condensing discharged steam may be provided in a gas-discharge pipe connected to the inner can and the jacket portion.

According to the configuration, since the discharged steam is condensed, the gas-discharge speed can be increased and thereby a gas-discharging time can be reduced.

Advantageous Effects of Invention

According to the steam sterilizer of the present invention, it is possible to achieve an appropriate temperature distribution while reducing a sterilization operation time.

DESCRIPTION OF EMBODIMENTS

First Embodiment

A steam sterilizer according to the present embodiment will be described with reference to the drawings below.

Figure 1:
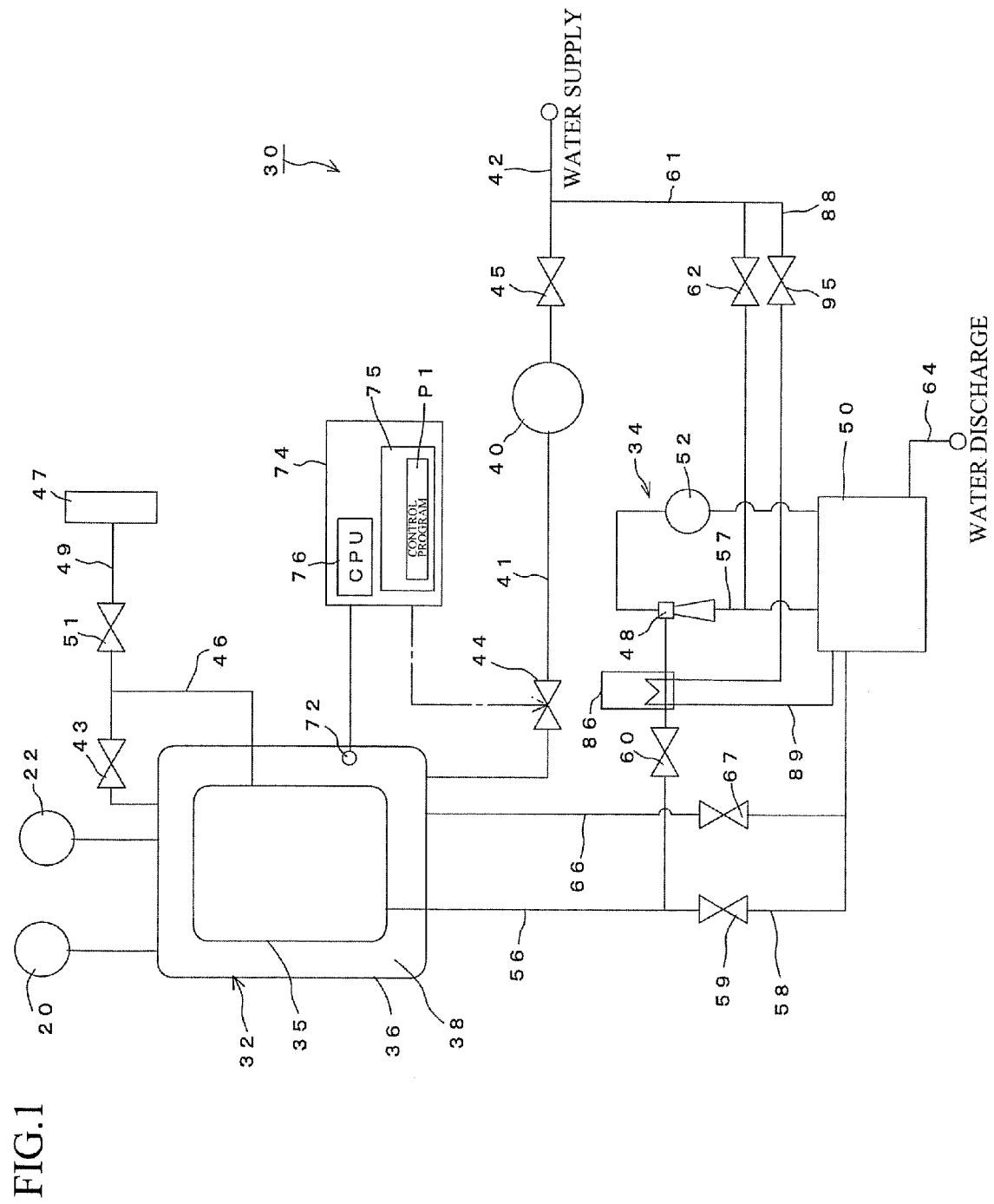
FIG. 1 is a schematic line diagram of a first embodiment of a steam sterilizer.

FIG. 1 is a schematic line diagram of a first embodiment of a steam sterilizer. Meanwhile, the steam sterilizer of the present embodiment adopts a configuration in which the sterilization tank is used as an inner portion of the inner can of the pressure vessel having the double-can structure.

A steam sterilizer 30 includes a pressure vessel 32 housing an object to be sterilized and a vacuum-generating means 34 that is connected to the pressure vessel 32 and that brings the inside of the pressure vessel 32 into a vacuum state.

The pressure vessel 32 has a double-can structure including an inner can 35 and an outer can 36, and a gap therebetween is a jacket portion 38. Inside the inner can 35, objects to be sterilized including a bandage, a scalpel, a pair of forceps, and a surgical gown are housed. The saturated steam described below is introduced into the jacket portion 38, and a wall surface of the inner can 35 is heated up to a predetermined temperature, and then the temperature can be maintained.

A steam-supplying pipe 41 for introducing the saturated steam generated by a steam-generating device 40 is connected to the jacket portion 38. The steam-supplying pipe 41 includes a steam-supplying pipe valve 44 that opens and closes the steam-supplying pipe 41 to control the introduction of saturated steam into the jacket portion 38.

According to the present embodiment, the steam-generating device 40 includes an electric heater for heating water, and water piping 42 for supplying the water from an outside is connected to the steam-generating device 40. Furthermore, the water piping 42 includes a water-supply valve 45 capable of opening and closing the water piping 42 in order to control the supply of the water to the steam-generating device 40.

The steam-supplying pipe 41 adopts the diameter that allows the pressure-increase rate at 100 kPa/min or more in the inner can 35. Meanwhile, preferably, the pressure-increase rate is 150 kPa/min~300 kPa/min. In addition, the faster the pressure-increase rate is, the more preferable it is, but when the speed is 1000 kPa/min or more, a packing material for protecting the object to be sterilized, generally used in hospitals or the like at present, from contamination after the sterilization may be damaged, and thus the pressure-increase rate is desirably less than 1000 kPa/min.

Incidentally, the pressure-increase rate greatly varies depending on the combination of the diameter of the steam-supplying pipe 41, and a volume, a shape and the like of the pressure vessel 32. Therefore, since the diameter varies depending on the corresponding pressure vessel 32, the pressure-increase rate and the diameter of the steam-supplying pipe 41 have a one-to-one relationship.

Meanwhile, as to the supply of the water to the steam-generating device 40, processed water such as soft water or Reverse Osmosis (RO) water may be supplied to the steam-generating device 40 in order to reduce scale adhering onto an inside of the steam-generating device 40. In such a case, the water piping 42 through which the water is supplied from the outside may be divided into two systems, and the piping may be connected so as to supply the processed water to the primary side of the water-supply valve 45 (not illustrated).

The pressure vessel 32 is provided with connection pipe 46 for connecting the jacket portion 38 with the inner can 35 in order to supply the saturated steam in the jacket portion 38 into the inner can 35. A connection-pipe valve 43 for controlling the supply of the saturated steam into the inner can 35 is provided at a middle portion of the connection pipe 46.

Furthermore, an air-supply pipe 49 capable of supplying air via an air filter 47 is connected at the middle portion of the connection pipe 46. A portion of the air-supply pipe 49 before the connection to the connection pipe 46 is provided with an air-supply valve 51 for controlling the supply of air.

The vacuum-generating means 34 according to the present embodiment includes a water ejector 48, a tank 50 for storing the supply water supplied from the outside, and a pump 52 for supplying the supply water in the tank 50 to the water ejector 48.

The water ejector 48 can adopt a generally known configuration. The water ejector 48 according to the present embodiment includes a nozzle formed in a T-like shape (not illustrated), and the water pressurized by the pump 52 is introduced into a nozzle inlet (an upper edge portion of the water ejector 48 illustrated in FIG. 1).

A flow path diameter of the nozzle constituting the water ejector 48 becomes thinner in the middle portion going from the inlet to an outlet (a lower edge portion of the water ejector 48 illustrated in FIG. 1), and a gas and water-discharge pipe 56 (gas and water-discharge pipe in the inner can 35) from the pressure vessel 32 is connected to the thin diameter portion.

When the water pressurized by the pump 52 is supplied into the introduction of the nozzle constituting the water ejector 48, at a portion having the thin nozzle, a flow speed becomes larger according to a principle of Venturi, and thus the discharge gas from the pressure vessel 32 is sucked via the gas and water-discharge pipe 56.

At the outlet of the nozzle of the water ejector 48, a water-discharge pipe 57 connected to the tank 50 is provided. In the water-discharge pipe 57, the water from the tank 50 that has passed through the nozzle, and the air and the water discharged from the gas and water-discharge pipe 56 are circulated. Therefore, the water that is a working fluid of the water ejector 48 can return to tank 50 via the water-discharge pipe 57, and the discharge gas and the discharge water from the pressure vessel 32 can also be stored in the tank 50.

The gas and water-discharge pipe 56 from the inner can 35 of the pressure vessel 32 is provided with a branch pipe 58 that is branched from the pipe connected to the water ejector 48 described above and that is directly connected to the tank 50.

On a side of the branch pipe 58 and on a side connected to the water ejector 48 of the gas and water-discharge pipe 56, valves 59 and 60 capable of opening/closing each pipe are provided respectively. By an opening/closing action of the valves 59 and 60, not only is the inside of the inner can 35 drawn to a vacuum, but also the water discharge can be directly carried out from the inner can 35 to the tank 50.

A branch pipe 61 branched from the water piping 42 is connected to the tank 50, and the water from the outside is supplied to the tank 50 and is stored therein. The middle portion of the branch pipe 61 is provided with a valve 62 for opening/closing the branch pipe 61.

In addition, the tank 50 is provided with a water-discharge pipe 64, and the water in the tank 50 can be discharged.

According to the present embodiment, the branch pipe 61 of the water piping 42 for supplying the water from the outside into the tank 50 is connected to the water-discharge pipe 57 on a discharge side of the water ejector 48. As described above, the branch pipe 61 for supplying the water to the tank 50 is connected to the water-discharge pipe 57 of the water ejector and thus water-hammer action is prevented. More specifically, when the steam from the inner can 35 is discharged into the tank 50 as it is, the steam is rapidly cooled down and condensed in the tank 50, and the pressure is decreased. Accordingly, the decrease of pressure and the rapid supply of water into the tank 50 cause shock and noise. However, since the branch pipe 61 for supplying the water is connected to the water-discharge pipe 57 of the water ejector 48, the water from the branch pipe 61 is forcibly supplied to the water-discharge pipe 57 by an action of the water ejector 4. Therefore, according to this configuration, the steam discharged in the water-discharge pipe 57 can be condensed and the water-hammer action can be prevented.

Furthermore, a drain-discharge pipe 66 for discharging drain in the jacket portion 38 is connected to the tank 50.

The drain-discharge pipe 66 is provided with a steam trap 67 to discharge only the drain from atmosphere including the steam, so as not to discharge the steam from the drain-discharge pipe 66 as much as possible.

As described above, the gas and water-discharge pipe 56 from the inner can 35 and the drain-discharge pipe 66 of the jacket portion 38 are connected to the tank 50 to thereby collect all the discharge gas and water from the pressure vessel 32 into the tank 50. In addition, since the water is supplied from the outside into the tank 50 via the branch pipe 61 of the water piping 42 as described above, the high-temperature discharge gas and water from the pressure vessel 32 is cooled down to a predetermined temperature. Therefore, unlike the conventional devices, even without providing the processing device of the discharged gas and water at the high temperature, the tank for supplying the water to the water ejector 48 can also perform a cooling process on the discharged gas and water at the high temperature.

The gas and water-discharge pipe 56 for circulating the discharge gas and water from the pressure vessel 32 that is to be introduced to the water ejector 48 is provided with condensing means 86 for condensing the steam in the discharge gas. By condensing the gas, a gas-discharge speed can be speeded up.

As the condensing means 86 according to the present embodiment, a heat exchanger is adopted. Any heat exchanger may be adopted. A heat exchanger of a plate type is adopted herein which exchanges heat by alternately circulating a high-temperature fluid and a low-temperature fluid among plates having a plurality of layers.

The heat exchanger 86 includes a high-temperature fluid inlet port for introducing the discharge gas at a high temperature from pressure vessel 32 and a low-temperature fluid inlet port for introducing the fluid at a lower temperature than the discharged gas at the high temperature, to thereby exchange the heat between the high-temperature fluid and the low-temperature fluid.

According to the present embodiment, as the low-temperature fluid to be introduced into the heat exchanger 86, the water from the outside into the tank 50 is used. Specifically, similarly to the branch pipe 61 connected to the tank 50, a branch pipe 88 is provided at the middle portion of the water piping 42, and the branch pipe 88 is connected to the low-temperature fluid inlet of the heat exchanger 86, and then the water from the outside is used for exchanging the heat as the fluid at the low temperature. Furthermore, a middle portion of the branch pipe 88 is provided with a valve 95 in order to control the supply of the water to the heat exchanger 86.

Moreover, the water whose temperature is risen after the heat has been exchanged by the heat exchanger 86 is introduced into the tank 50 through piping 89.

The discharge gas from the pressure vessel 32 cooled down after having passed through the heat exchanger 86 is introduced into a middle portion of the nozzle of the water ejector 48 in a state of the steam being condensed.

As described above, since the steam in the discharge gas from the pressure vessel 32 is condensed in a previous stage where the steam is sucked into the water ejector 48, much consideration does not have to be taken that the steam comes into contact with the water by the water ejector 48 to thereby be condensed. Namely, even if the temperature of the water supplied from the tank 50 to the water ejector 48 is high (for example, approximately 40° C. to 60° C.), the gas-discharge speed and a vacuum-reaching level is not adversely affected. With this arrangement, in order to lower the temperature of the water housed in the tank 50, a great amount of water does not need to be introduced via water piping 96, and thus an amount of water usage can be saved.

Meanwhile, the configuration for condensing the steam in the discharge gas of the pressure vessel 32 before the introduction of the steam to the water ejector 48 is not limited to the above-described heat exchanger.

For example, the above-described heat exchanger may be of a fin type, and may have any configuration as long as it has a configuration for being able to condense the steam in the gas.

In the jacket portion 38, a jacket-portion temperature sensor 72 of the jacket portion for measuring the temperature inside the jacket portion 38 is provided.

Data of the temperature measured by the jacket-portion temperature sensor 72 is input to a control unit 74.

The control unit 74 includes a memory 75 such as a read only memory (ROM) and a random access memory (RAM), and a processor 76 such as a central processing unit (CPU), and executes action control of the steam sterilizer 30 according to the present embodiment. The memory 75 previously records a control program P1, and the processor 76 performs a control action on the basis of the control program P1.

Figure 2:
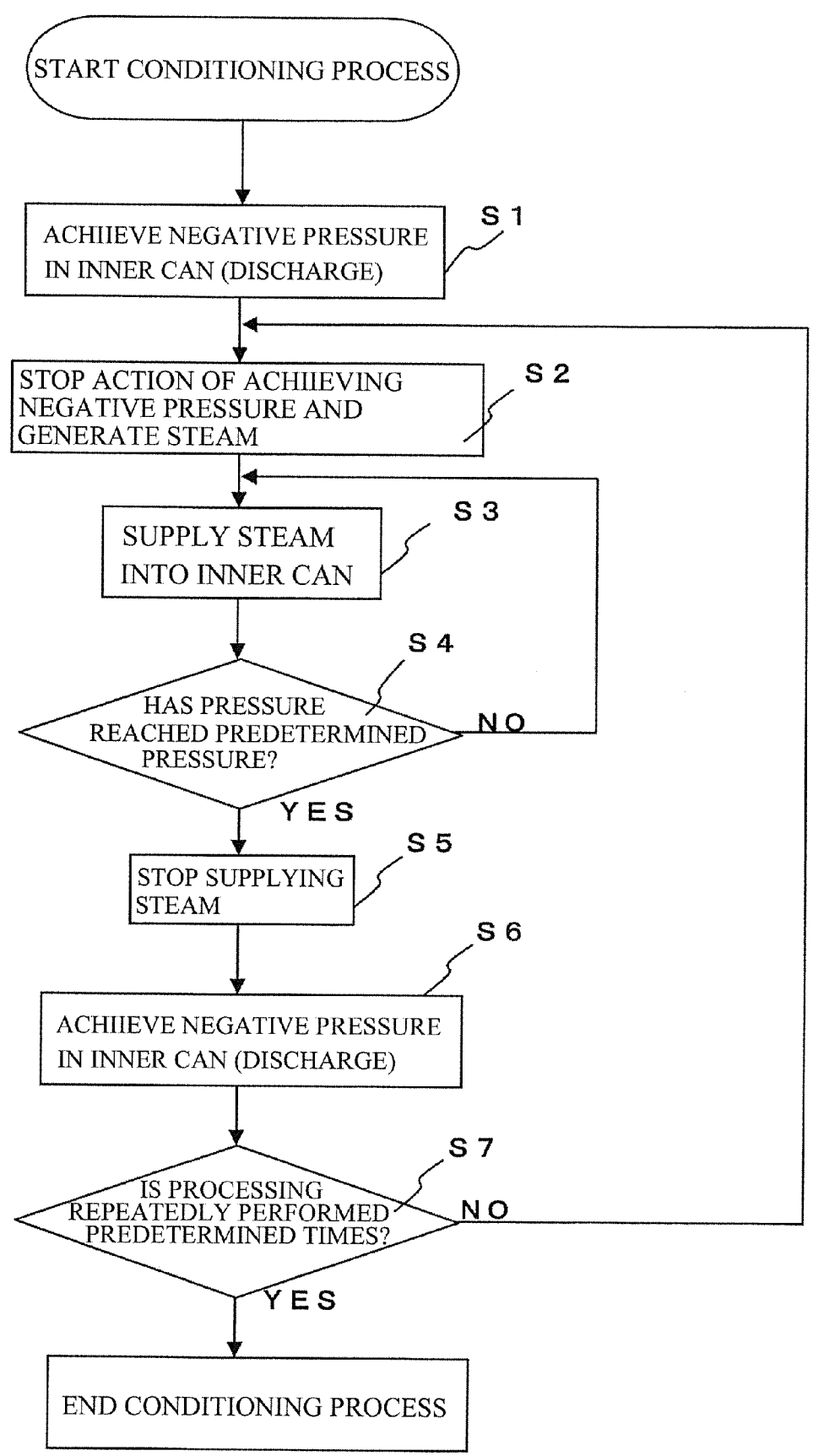
FIG. 2 is a flowchart illustrating an action of a conditioning process of the first embodiment.

Hereinafter, on the basis of a flowchart illustrated in FIG. 2, the action control of the steam sterilizer executed by the control unit will be described.

As a previous stage of the sterilization process, a conditioning process is executed. The conditioning process eliminates the air inside the inner can 35 before the introduction of the stream in the sterilization process.

First, the control unit 74 drives the vacuum-generating means 34 to thereby achieve a negative pressure in the inner can 35 (step S1). Next, the control unit 74 stops an action of the vacuum-generating means 34 and drives the steam-generating device 40 to generate the steam (step S2).

In addition, the control unit 74 fully opens the steam-supplying pipe valve 44 and the connection-pipe valve 43 to introduce the steam generated by the steam-generating device 40 into the jacket portion 38 (step S3). In step S3, the steam is introduced from the jacket portion 38 into the inner can 35 via the connection pipe 46.

On the basis of data of pressure of a pressure sensor (not illustrated) for detecting a pressure inside the inner can 35, the control unit 74 determines whether or not the pressure inside inner can 35 has reached a predetermined pressure value previously set (for example, a value that is slightly lower than the pressure value at the time of the sterilization process) (step S4). When it is determined that the pressure has reached the predetermined pressure value, the steam-supplying pipe valve 44 is completely closed and the introduction of the steam is stopped (step S5).

In addition, the control unit 74 drives the vacuum-generating means 34 and discharges the steam inside the inner can 35 to thereby achieve the negative pressure therein (step S6).

As in steps S1 to S6, the control unit 74 repeats cycles of achieving the negative pressure, supplying the steam, and discharging the steam a predetermined number of times previously set (step S7). As described above, the repetition of achieving the negative pressure, supplying the steam, and discharging the steam makes it possible to eliminate the air inside the inner can 35.

As described above, according to the present embodiment, since the steam generated is introduced into the inner can 35 via the jacket portion 38 without controlling the pressure-increase rate, a time for the conditioning process can be decreased.

Figure 3:
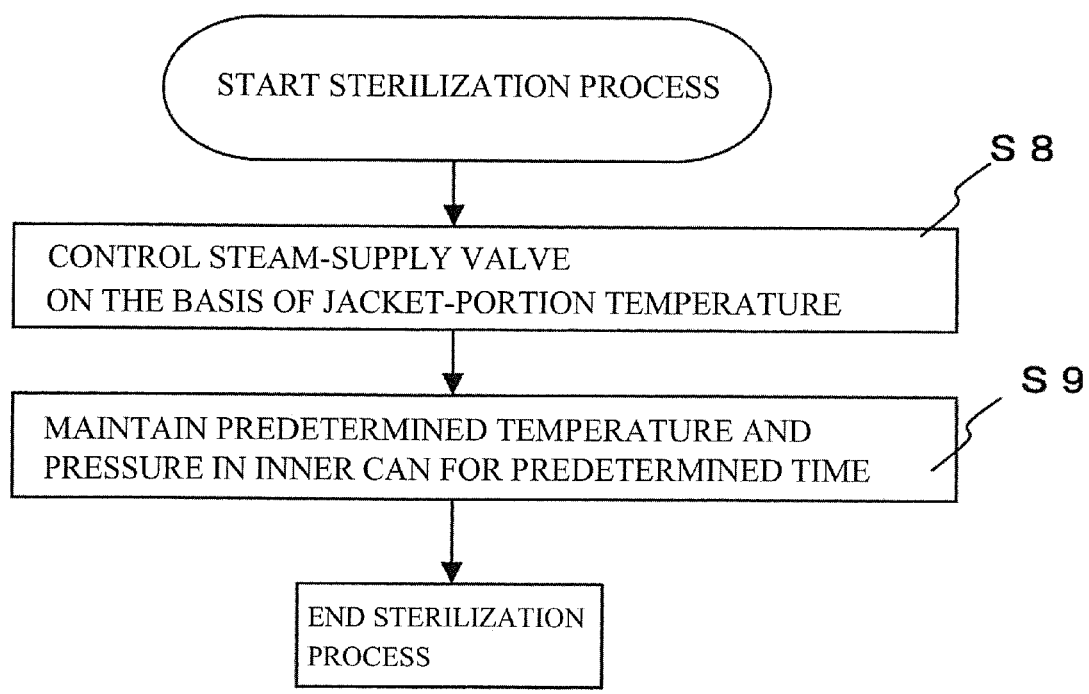
FIG. 3 is a flowchart illustrating an action of a sterilization process of the first embodiment.

After the completion of the conditioning process, the process proceeds to the sterilization process. FIG. 3 illustrates a flowchart of the sterilization process.

On the basis of the temperature data detected by the jacket-portion temperature sensor 72, the control unit 74 supplies the steam while controlling a level of opening the steam-supplying pipe valve 44 (step S8). That is, the control unit 74 controls the steam-supplying pipe valve 44 so as to set the inside of the jacket portion 38 to be at the temperature that has been previously set along with elapse of the time after the start of the sterilization process. Namely, unlike in the conditioning process in which the steam is introduced as rapidly as possible, in the sterilization process, the steam is introduced in such a manner that the temperature gradually becomes a predetermined sterilization temperature. Meanwhile, the control unit 74 fully opens the connection-pipe valve 43 also at the time of the sterilization process.

When the temperature of the jacket portion reaches the predetermined temperature, the control unit 74 maintains the predetermined temperature and pressure inside the inner can 35 for a predetermined time, to thereby perform the sterilization on the object to be sterilized therein (step S9).

As described above, on the basis of the temperature inside the jacket portion 38, the temperature-rising rate therein is controlled, and further full opening of the connection-pipe valve 43 in supplying the steam from the jacket portion 38 to the inner can 35 prevents the generation of the overly heated steam, and thus a preferable temperature distribution can be set in the inner can 35.

The description on this point will be given below. It is clarified that, in order to achieve the preferable temperature distribution, a speed for supplying the steam should not be very fast. Namely, this is because when the steam-supply speed is fast, an overshoot exceeding the sterilization temperature or the sterilization pressure may occur, and when the increase in the pressure in the jacket portion makes larger the pressure difference between the inside of the inner can and that of the jacket portion to thereby speed up the steam-supply speed, the steam supplied into the jacket portion having a high pressure turns out to be the overly heated steam. Additionally, the overly heated steam is inferior to the saturated steam in sterilization ability.

On the other hand, the sterilization time is also desired to be reduced. Since the steam-supply speed needs to be increased in order to reduce the sterilization time, the requests to reduce the sterilization time and to obtain the preferable temperature distribution conflict with each other.

However, like in the present embodiment, the connection-pipe valve 43 is fully opened at the time of the sterilization process, the jacket portion 38 and the inner can 35 are considered as one body, and the supply of the steam to the jacket portion 38 is controlled such that the steam-supply speed is not too fast, and thus the generation of the overly heated steam can be prevented while the stable temperature distribution is attempted.

A control method of the steam-supplying pipe valve 44 includes both of a case of adjusting an opening angle of the valve such as a proportion control valve, and a case of adjusting an opening/closing time of the valve such as an on and off valve.

Namely, any control method may be adopted as long as an amount of the steam to be supplied from the steam-supplying pipe can be adjusted. Regarding this point, the same also applies to the following embodiment.

Second Embodiment

Hereinafter, the second embodiment of the present invention will be described.

Meanwhile, the same reference symbols are attached to the same constituent elements as those in the first embodiment described above, and the description may be omitted.

The second embodiment is different from the first embodiment in that the control of the steam-supplying pipe valve is performed on the basis of the temperature difference between the jacket portion and the inner can at the time of the sterilization.

Figure 4:
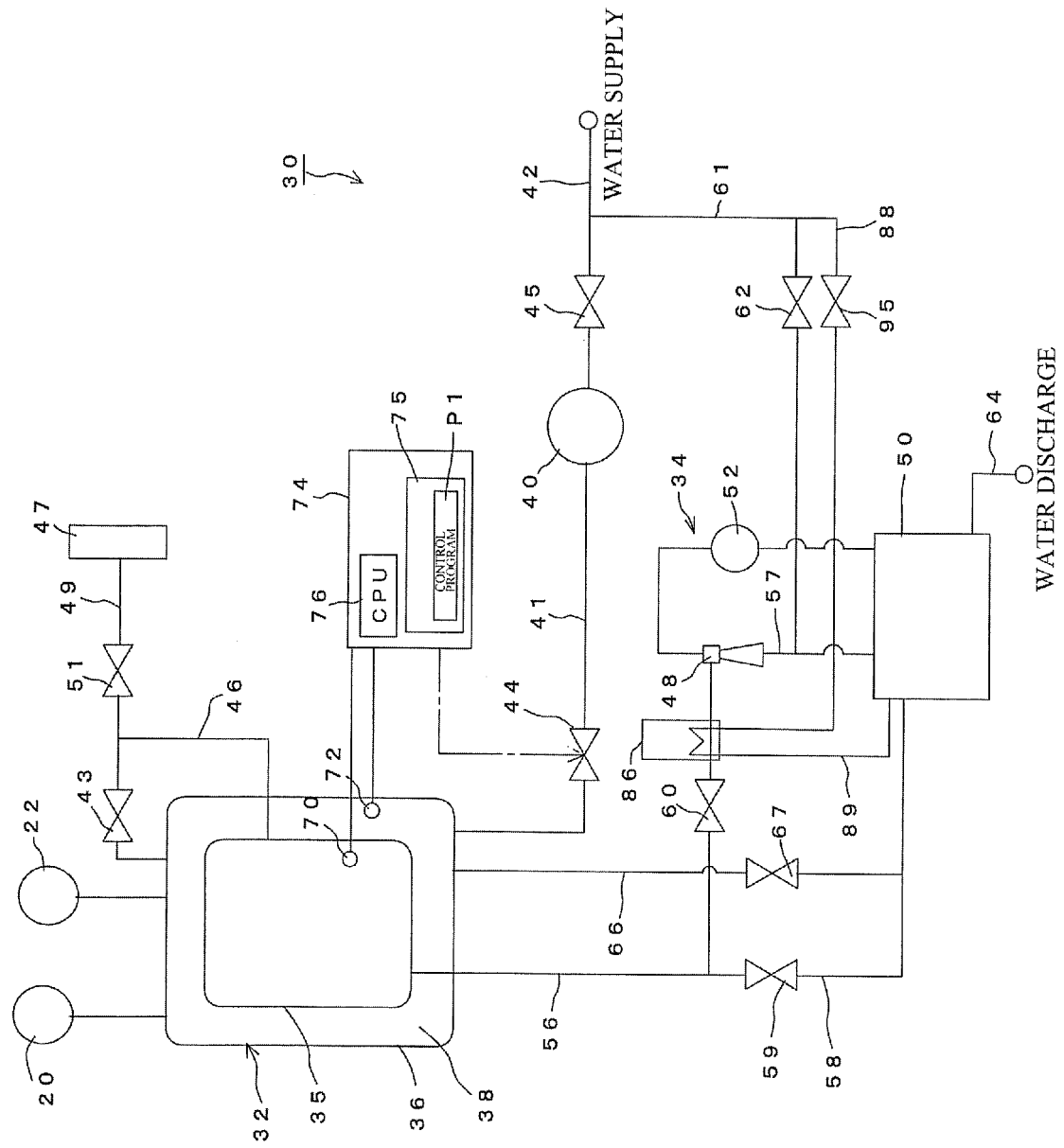
FIG. 4 is a schematic line diagram of a second embodiment of a steam sterilizer.

Namely, as illustrated in FIG. 4, according to the present embodiment, an inner can temperature sensor 70 for measuring the temperature in the inner can 35 is provided and the temperature data measured by the inner-can temperature sensor 70 is input to the control unit 74.

Hereinafter, the operation control of the steam sterilizer performed by the control unit according to the present embodiment will be described.

First, as the previous stage of the sterilization process, the conditioning process is performed. The conditioning process is a process for eliminating the air in the inner can 35 before the introduction of the steam in the sterilization process. The conditioning process has the same control content as that illustrated in FIG. 2, and thus the description is omitted here.

Figure 5:
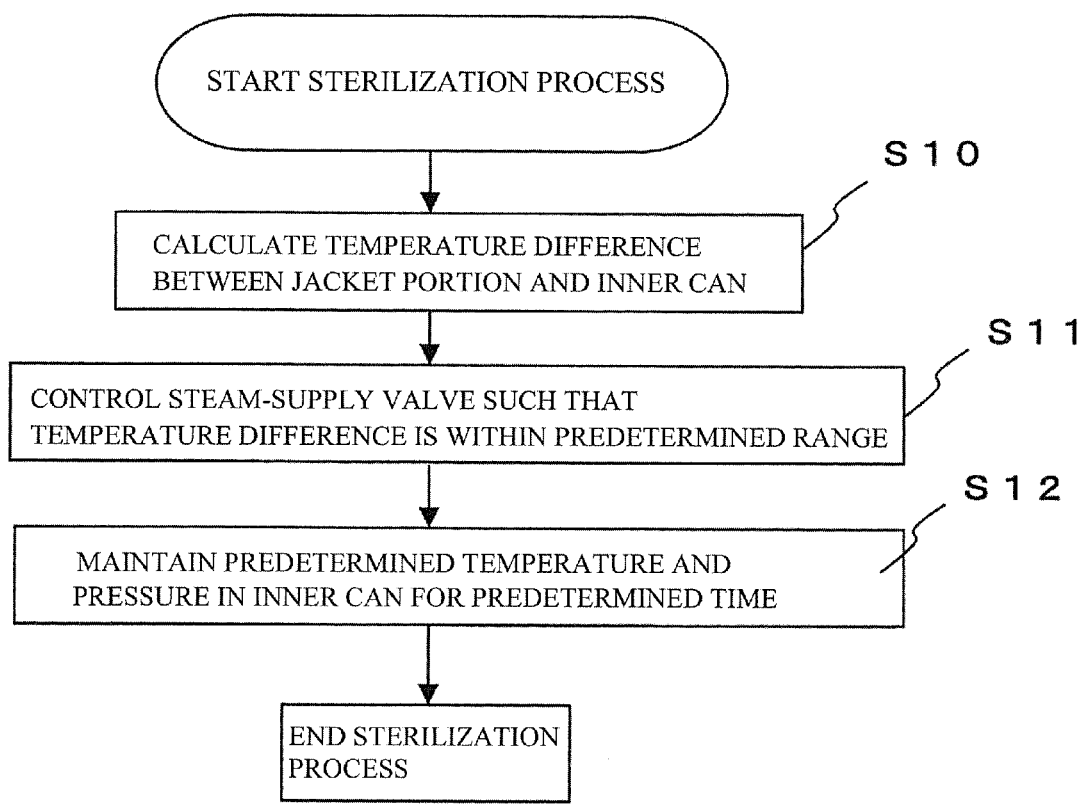
FIG. 5 is a flowchart illustrating an action of the sterilization process of the second embodiment.

The control unit 74 proceeds to the sterilization process after the completion of the conditioning process. FIG. 5 illustrates a flowchart of the sterilization process.

In the sterilization process according to the present embodiment, the control unit 74 calculates difference of the temperature data detected by the inner-can temperature sensor 70 and the temperature data detected by the jacket-portion temperature sensor 72 (step S10). In addition, the control unit 74 supplies the steam while controlling the level of opening the steam-supplying pipe valve 44 such that the temperature difference between the jacket portion 38 and the inner can 35 is within a predetermined range previously set (step S11). The control unit 74 fully opens the connection-pipe valve 43 also at the time of the sterilization process.

Namely, the control unit 74 controls the steam-supplying pipe valve 44 such that the temperature difference between the jacket portion 38 and the inner can 35 is minimal. With this arrangement, the jacket portion 38 and the inner can 35 are considered as the one body and the temperature difference between the jacket portion 38 and the inner can 35 is reduced, and thus the temperature-rising rate in the jacket portion 38 can be controlled and the rise of the temperature of the jacket portion 38 is prevented, whereby the generation of the overly heated steam can be prevented when the steam is supplied to the jacket portion 38. In addition, it is possible to achieve the preferable temperature distribution in the inner can 35, by controlling the temperature-rising rate.

When the temperature of the jacket portion reaches the predetermined temperature, the control unit 74 maintains the predetermined temperature, the predetermined pressure for the predetermined time in the inner can 35 to thereby perform the sterilization on the object to be sterilized in the inner can 35 (step S12).

As described above, the control of the temperature-rising rate in the jacket portion 38 is performed to thereby reduce the temperature difference between the jacket portion 38 and the inner can 35, and further the steam is supplied from the jacket portion 38 into the inner can 35 with the connection-pipe valve 43 fully opened, and thus the generation of the overly heated steam can be prevented and the preferable temperature distribution can be realized in the inner can 35.

Other Embodiment

In each present embodiment, there has been described the case where the steam is generated by the steam-generating device 40.

However, a configuration may also be adopted in which the steam generator is not provided and the saturated steam is supplied into the pressure vessel 32 from the outside of the steam sterilizer 30 through the steam-supplying pipe 41. As an outer device to which the steam-supplying pipe 41 is connected, any device can be used as long as the saturated steam is generated.

Furthermore, the vacuum-generating means may be not only means of using vacuum pump, but also means of adopting the water ejector.

However, the vacuum-generating means of using the water ejector can more easily condense the steam by making contact with the pressurized water from the tank 50 in the water ejector 48. Therefore, the use of the water ejector 48 as the vacuum-generating means makes it possible to speed up the gas-discharge speed.

What is claimed is:

1. A steam sterilizer comprising:
 a sterilization tank configured to house an object to be sterilized and perform sterilization on the object to be sterilized by maintaining supplied steam at a predetermined temperature and a predetermined pressure;
 a steam-supplying pipe configured to supply the steam into the sterilization tank;
 a steam-supplying pipe valve configured to control an amount of steam flow flowing through the steam-supplying pipe, wherein said steam-supplying pipe is provided so as to have a diameter that allows a pressure-increase rate of 100 kPa/min or more in the sterilization tank;
 a control unit configured to control said steam-supplying pipe valve to be fully opened, in a conditioning process for repeatedly performing introduction and discharge of the steam in and from the sterilization tank and to control said steam-supplying pipe valve so as to supply a predetermined amount of steam in a sterilization process after the conditioning process, wherein said sterilization tank is defined by an inner can of a pressure vessel having a double-can structure including the inner can and an outer can;

a jacket portion is provided between the inner can and the outer can;

said steam-supplying pipe is connected so as to introduce the steam into the jacket portion;

a connection pipe for connecting the jacket portion with the inner can is provided in order to introduce, into said inner can, the steam introduced into the jacket portion;

a connection-pipe valve for controlling an amount of steam flow flowing through the connection pipe is provided;

a jacket portion temperature sensor is provided for measuring an inner temperature of said jacket portion, and wherein, in a sterilization process after the conditioning process, said control unit is configured to control said steam-supplying pipe valve on the basis of the temperature detected by said jacket portion temperature sensor.

2. The steam sterilizer according to claim 1,
wherein, in the sterilization process after the conditioning process, said control unit is configured to fully open said connection-pipe valve.

3. The steam sterilizer according to claim 2,
wherein a condensing device for condensing discharged steam is provided in a gas-discharge pipe connected to said inner can and said jacket portion.

4. The steam sterilizer according to claim 1,
wherein a condensing device for condensing discharged steam is provided in a gas-discharge pipe connected to said inner can and said jacket portion.

5. A steam sterilizer comprising:
a sterilization tank configured to house an object to be sterilized and perform sterilization on the object to be sterilized by maintaining supplied steam at a predetermined temperature and a predetermined pressure;

a steam-supplying pipe configured to supply the steam into the sterilization tank;

a steam-supplying pipe valve configured to control an amount of steam flow flowing through the steam-supplying pipe, wherein said steam-supplying pipe is provided so as to have a diameter that allows a pressure-increase rate of 100 kPa/min or more in the sterilization tank;

a control unit configured to control said steam-supplying pipe valve to be fully opened, in a conditioning process for repeatedly performing introduction and discharge of the steam in and from the sterilization tank and to control said steam-supplying pipe valve so as to supply a predetermined amount of steam in a sterilization process after the conditioning process, wherein said sterilization tank is defined by an inner can of a pressure vessel having a double-can structure including the inner can and an outer can;

a jacket portion is provided between the inner can and the outer can;

said steam-supplying pipe is connected so as to introduce the steam into the jacket portion;

a connection pipe for connecting the jacket portion with the inner can is provided in order to introduce, into said inner can, the steam introduced into the jacket portion;

a connection-pipe valve for controlling an amount of steam flow flowing through the connection pipe is provided;

an inner can temperature sensor for measuring an inner temperature of the inner can is provided;

a jacket portion temperature sensor is provided for measuring an inner temperature of said jacket portion, and wherein, in the sterilization process after the conditioning process, said control unit is configured to control said steam-supplying pipe valve such that temperature difference between a temperature detected by said inner can temperature sensor and a temperature detected by said jacket portion temperature sensor is within a predetermined range.

6. The steam sterilizer according to claim 5,
wherein, in the sterilization process after the conditioning process, said control unit is configured to fully open said connection-pipe valve.

7. The steam sterilizer according to claim 5,
wherein a condensing device for condensing discharged steam is provided in a gas-discharge pipe connected to said inner can and said jacket portion.

8. The steam sterilizer according to claim 6,
wherein a condensing device for condensing discharged steam is provided in a gas-discharge pipe connected to said inner can and said jacket portion.

* * * * *